United States Patent [19]

Bruno

[11] Patent Number: 4,801,013
[45] Date of Patent: Jan. 31, 1989

[54] CONTAINMENT DEVICE FOR SAFELY REMOVING, STORING AND ULTIMATELY DISPOSING OF NEEDLES FROM HYPODERMIC NEEDLE/SYRINGE ASSEMBLIES

[76] Inventor: John Bruno, 77-83 Second Ave., Paterson, N.J. 07514

[21] Appl. No.: 12,949

[22] Filed: Feb. 10, 1987

[51] Int. Cl.$^4$ .................. B65D 25/00; B65D 51/00
[52] U.S. Cl. .................................................. 206/366
[58] Field of Search ................................. 206/366, 365

[56] References Cited

U.S. PATENT DOCUMENTS

| | | | |
|---|---|---|---|
| 4,351,434 | 9/1982 | Elisha | 206/366 |
| 4,375,849 | 3/1983 | Hanifi | 206/366 |
| 4,452,358 | 6/1984 | Simpson | 206/366 |
| 4,453,648 | 6/1984 | Harris | 220/324 |
| 4,466,538 | 8/1984 | Gianni | 206/366 |
| 4,485,918 | 12/1984 | Mayer | 206/366 |
| 4,488,643 | 12/1984 | Pepper | 206/366 |
| 4,494,652 | 1/1985 | Nelson et al. | 206/366 |
| 4,576,281 | 3/1986 | Kirksey | 206/366 X |

OTHER PUBLICATIONS

Brochure of "SHARPS-tainer" device made by Winfield Corp. of San Diego, Calif.
Brochure of disposal systems (#8900 and 8700 series) made by Sage Products Inc. of Cary, Ill.

*Primary Examiner*—William Price
*Attorney, Agent, or Firm*—Morgan & Finnegan

[57] ABSTRACT

A needle removal and storage device for removing needles from hypodermic needle/syringe assemblies and automatically receiving and safely storing removed needles within the device. The device includes a storage/containment member closed at one end and proportioned to receive used needles, and a top assembly at the open end of the storage/containment member which provides an opening to receive a needle in its hub portion. The top assembly is provided with a pair of grasping members mounted to generally opposite sides of the storage/containment member at its open end. The grasping members are adapted to receive the needle hub portion of a needle/syringe assembly and grasp the hub portion when squeezed together to permit removal of the needle from the syringe. The storage/containment member is generally flexible and resilient at its open end to permit the grasping members to be squeezed together so as to constrict the opening in the top assembly and grasp the needle hub at its ribbed portion for removal of the needle from the syringe, yet resiliently bias the grasping members away from each other after the grasping force is released to allow the needle to drop vertically into the storage/containment member, needle point first. The device further includes a closure member formed integrally with one of the grasping members via a living hinge-type connection. The closure member is adapted to releasably engage the other grasping member so as to hold the closure member securely closed over the open end of the storage/containment member when the device is not being used for removal of a needle.

17 Claims, 3 Drawing Sheets

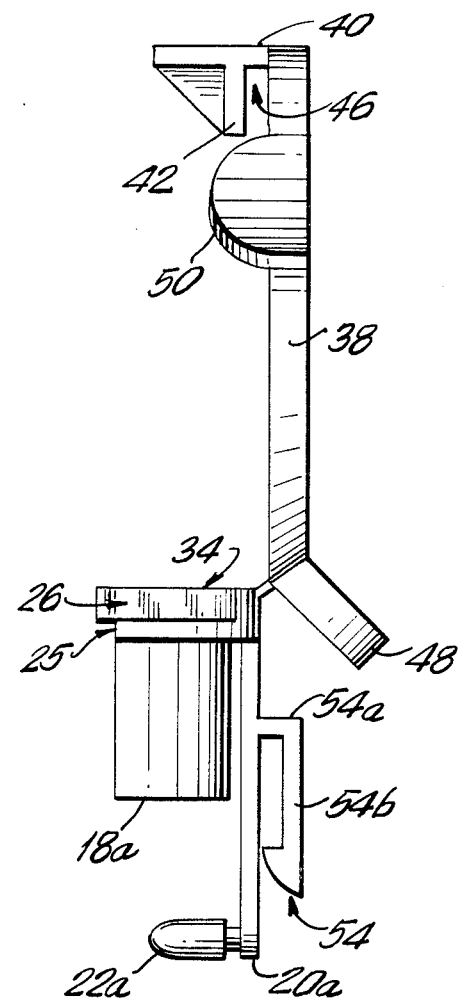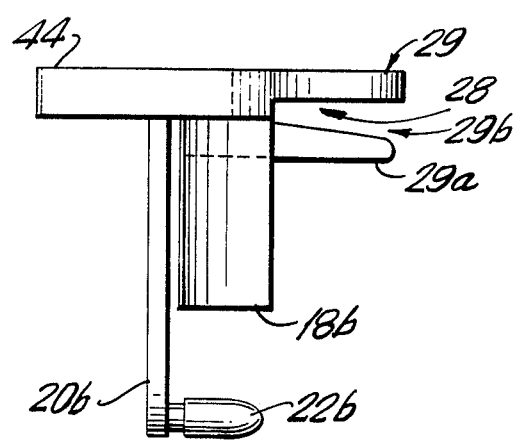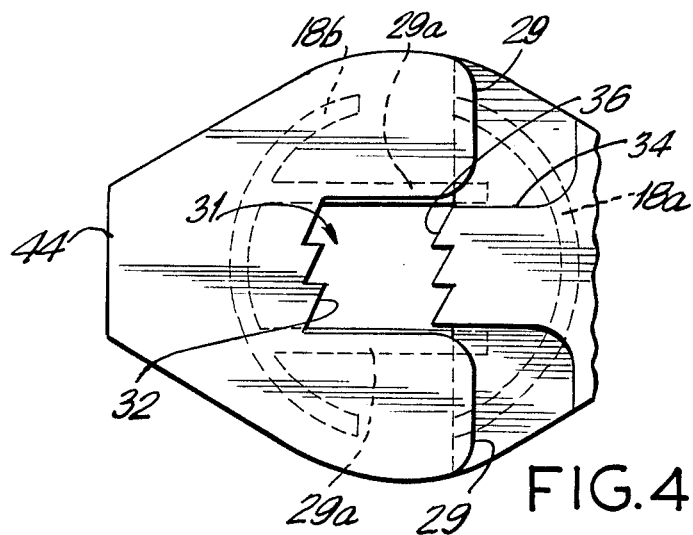

CONTAINMENT DEVICE FOR SAFELY REMOVING, STORING AND ULTIMATELY DISPOSING OF NEEDLES FROM HYPODERMIC NEEDLE/SYRINGE ASSEMBLIES

BACKGROUND AND OBJECTS OF THE INVENTION

The present invention relates generally to devices for safely removing the needle portions from hypodermic needle/syringe assemblies, and, more particularly, to a device which enables safe removal of needles from needle/syringe assemblies and also automatically provides safe storage of the needles until the entire device, needles and all, are transmitted for ultimate disposal, substantially without risk of puncture by or contact with the needles during removal, storage or disposal.

With the widespread use of disposable medical implements, particularly hypodermic needles, a definite need has developed for ways to safely handle and dispose of such implements after use without risk of exposing any person handling the devices to injury, infection or disease by puncture or contact with the used needle. The tragic outbreak of the highly contagious AIDS disease has dramatically highlighted the need for safer handling, storage and disposal of such implements.

In the case of disposable hypodermic needles, it had once been common practice to break or cut the needle portions after use before discarding the needle and syringe. The purpose of this procedure was to reduce the size of the overall needle/syringe assembly and to eliminate the sharp point from the needle to reduce the risk of puncture, scratching or other injury which might otherwise result from handling. In breaking or cutting the needles, however, a substantial danger existed that accidental puncture might occur during the breaking or cutting operation, thus exposing the holder to possible injury and, further, to possible infection or disease as a result of such puncture In addition, residual medication in the needle can splatter onto the person or his clothes, and, potentially harmful fumes from the residual medication could be inhaled as a result of the so-called aerosol effect. Furthermore, the blades of the cutting tool are now recognized as a breeding ground for germs, bacteria and other disease-causing micro-organisms to which an unsuspecting person cutting the needle could be unnecessarily exposed.

Recently, an even greater danger has been recognized in connection with the handling and disposal of used needles as well as other sharp medical implements. It is now recognized that certain diseases, most notably Hepatitis B, can be transmitted by covert percutaneous—i.e., by merely contacting the contaminated needle or implement.

As a result of the foregoing dangers, it is preferred current practice to dispose of such devices intact, without dismantling them. However, in disposing of the whole hypodermic needle and syringe, the used needles were sometimes recapped before disposal with the same protective sheaths that were used during shipment from the manufacturer. The resheathing was intended to prevent possible injury while a person carries the needles to a suitable disposal unit. This practice itself, however, can result in accidental puncture or contact while the needle point is being resheathed. Because of this danger it is now recommended by the Center For Disease Control ("C.D.C.") that needles not be resheathed after use.

Although certain proposals have been advanced for eliminating some of the risks involved in the handling, storage and disposal of hypodermic needles and other sharp medical implements, they do not necessarily overcome all of the dangers. In fact, they themselves can become the source of other problems. For example, there are several specially designed containers for storing used hypodermic needles, at least one of which includes a "starburst" type opening through which the needle and syringe assemblies is passed into the container. However, the flaps created by the starburst opening can become a breeding ground for germs or infection due to the constant contact with the used needles. In other whole-needle disposal devices, there are generally no means for determining when the device is filled.

Although I have invented certain disposal devices (previously sold under the mark "D.D. Box" by D.D. Box, Inc. of Paterson, New Jersey and now sold by the American Hospital Supply Company) which overcome the foregoing and other dangers, there may still be instances where a disposal device for the whole needle/syringe assembly is not desired. For example, in emergency rooms, the urgency of a particular emergency situation may not permit time to seek out an appropriate disposal unit for the used needle/syringe assembly. In the absence of an immediately available disposal device it is likely that the used needle could be left lying unattended and unsecured, or an attempt might be made to resheath the needle. In either event, these are substantial risks of accidental puncture by or contact with contaminated needles.

Another place where a large disposal device might not be desired is in a doctor's office or in a home where persons inoculate themselves. A large capacity disposal unit may be impractical or undesirable because used implements would lay around too long before the device is filled and disposed of.

One approach for overcoming the foregoing difficulties involves removal of the needle from its syringe so that the syringe can be discarded with ordinary trash or refuse, while the needle (which is the only part having a significant risk of contamination) is placed in a storage receptacle until it can be properly disposed of. One device for practicing this method is sold under the name "SHARPStainer" by Winfield Corp. of San Diego Calif. This device includes a jar-like container with a snap-on lid to which is mounted a plier-like device for grasping a needle hub and unscrewing it from the syringe. When the plier-like device is opened, the needle falls into the jar. Although such device may provide adequate results, it still suffers several drawbacks. For example, it is relatively complicated and expensive to fabricate and the plier-like device can be broken off. The plier-like tool is also a separate member which must be molded and affixed to the jar top, thereby adding to the fabrication and assembly costs. The device is not convenient to carry around, and, it must be placed on a flat surface for successful operation which is still somewhat awkward to perform.

Another similar device is the "SHARPS COLLECTOR" sold by Becton Dickinson and Company of Rutherford, New Jersey. This device, too, includes a jar-like container with a snap-on lid. The lid further includes a separate disc-like member rotatably seated in the lid to allow circular movement when a needle is inserted into a slot formed in the disc and turned, plus, a separate cover member for closing the device. This device is relatively complicated to fabricate and assemble and must be placed on a flat surface for successful operation. Thus, it does not lend itself to convenient use (for example, the cover member must be snapped on and off each time the device is to be used) and the device cannot be conveniently carried around.

Accordingly, it is an object of the present invention to provide a new and improved device for safely handling used hypodermic needles. It is another object of the present invention to provide a new and improved device for safely handling used hypodermic needles, which provides both for safe and convenient removal of the needle from a needle/syringe assembly and for storage of the needles in a safe and durable receptacle until ultimate disposal can be made. It is also an object of the invention to provide such a device which is sturdy and constructed so as to be resistant to puncture by the needles stored therein, yet permits convenient and complete disposal of the needles together with the device.

It is also an object of the invention to provide a new and improved device for removal of needles from needle/syringe assemblies, and for subsequent safe storage of the removed needles, which prevents needles stored therein from falling out after they have been removed. It is another object of the invention to provide such a device which can be conveniently discarded in a larger storage/disposal device for used hypodermic needles or other disposable medical implements in an appropriate disposal facility. In addition, it is a further object of the invention to provide such a device for removing and storing needles from needle/syringe assembles, which is easily assemblable from component parts which are made by conventional fabrication techniques such as injection molding and extrusion processes.

It is yet a further object of the present invention to provide a new and improved device for removing needles from needle/syringe assemblies, and for subsequent storage of the separated needles, which is compact, and can be conveniently carried by medical personnel on their rounds. It is similarly an object of the invention to provide such a device which can be conveniently used in doctor offices or emergency rooms or in the homes of persons who give themselves injections of medications with needle assemblies having removable needles.

It is still another object of the invention to provide a new and improved device for removing needles from needle/syringe assemblies, and for subsequent safe storage of the separated needles, which includes reliable grasping means for securely grasping the needle hub to ensure reliable removal of the needle in a safe and relatively simple operation. It is a further object of the invention to provide such a device which provides for automatic storage of the needle once removed from the syringe portion simply by release of the grip imposed by the device on the needle hub. It is yet another object of the invention to provide such a device for removal and storage of hypodermic needles which permits ready identification of the filled condition.

It is yet a further object of the present invention to provide a new and improved device for removing needles from needle/syringe assemblies, and for subsequent safe storage of the separated needles, which can be carried in a shirt pocket or on a belt without danger of accidental puncture by or contact with needles stored therein. It is also an object of the invention to provide a device of the foregoing type which is adapted to permit relatively simple but secure closure of the device after each use and after it is filled to permit safe transport to the place of ultimate disposal The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises a device for the removal and storage, and ultimately, the disposal of the needle portion of a hypodermic needle/syringe assembly, which includes a relatively compact containment member adapted to store a plurality of needles separated from their syringe members and a top assembly mounted to the containment member for providing both a closure for the opening of the device and grasping means for grasping the needles to perform the removal operation. As preferably embodied, the containment member is a generally tubular member made from a relatively flexible material. The tubular containment member is closed at one end but open at the other, and the top assembly includes a pair of reciprocating grasping/closure members (hereinafter identified simply as "grasping members") mounted to the open end for enabling a person to grasp the hub of a needle between the grasping members simply by squeezing them together yet allow the needle to drop into the containment member when the person releases the grip on the grasping members. Advantageously, one of the grasping members includes a top cover which is hingedly mounted to the grasping member for closing off the open end of the containment member (and any spacing between the grasping members) when the device is not being used, but can be easily rotated to an open position when the device is to be used for needle removal. Advantageously, the top cover includes releasable locking means which snap closed when the cover is pushed down yet release relatively easily when use of the device is desired.

As preferably embodied, the containment member comprises a tube made of a generally flexible and resilient plastic material, and the grasping members are mounted on opposite sides of the open end of the tube so that the device automatically returns to its original tubular configuration as a result of the resilience of the tube material. Also as preferably embodied, the grasping members include oppositely disposed jaw-like segments for securely grasping a needle hub to be removed when squeezed together by a person using the device. The two grasping members advantageously have interfitting guide means for proper horizontal alignment of the grasping members during the hub-grasping and needle-removal operations to ensure reliable grip of the needle hub throughout these operations.

As preferably embodied, the guide means are in the form of a pair of projecting arm members on one grasping member and a pair of correspondingly proportioned recesses formed in the other, to accommodate slidable reciprocating relative movement of the grasping members. Advantageously, the arm members and recesses overlap each other even when the device is not being used for needle removal (i.e., when in its original, unsqueezed tubular configuration) to minimize the size of the opening created between the two grasping members. Further advantageously, one of the grasping members (preferably, the one with the pair of arm members) includes a pair of projecting leg members to maintain vertical alignment when the device in being used for needle removal to ensure that the grasping members do not jump out of alignment while a person is conducting the needle removal. The resultant two pairs of forks formed by the arm and leg members slidably receive the top wall of the other grasping member to maintain the same relative vertical alignment.

Also advantageously and as preferably embodied, the closure top is formed integrally as part of one of the grasping members and coupled thereto by a living hinge. A locking mechanism is advantageously formed between the closure top and the other grasping member for keeping the closure top secured when not in active use. In addition, a clip member may be formed on one of said grasping members for hanging the device from a person's pocket, belt or other portion of a garment. Further advantageously, a cup-like stand member may be provided to receive the tubular device and hold the device upright while, e.g., a person carries initial insertion of a needle point into the device, without requiring the device to be held in a person's hand, as recommended by C.D.C.

It will thus be appreciated by those skilled in the art that the objects and advantages specifically recited herein are achieved by the present invention as briefly described above and as more fully disclosed hereinafter. Thus, for example, by providing a device which, in a unitary structure, combines a hub-grasping means for separating a needle from its syringe and a containment member for receiving the needles it will be found that the handling of used hypodermic needle assemblies prior to complete disposal is relatively simple, convenient and safe. Similarly, by providing a tube-like containment member, the needle removal and storage device according to the invention is relatively compact and can be conveniently carried by medical personnel for ready use under virtually all circumstances, particularly in emergency situations. In addition, the tubular containment member provides for compact, vertical, side-by-side accumulation and storage of needles.

It will also be found that the needle removal/storage device according to the present invention requires relatively few parts to be assembled. The component parts can be fabricated by relatively conventional fabrication techniques (e.g., extrusion techniques for the tubing and injection molding techniques for the grasping members and the end plug which can be used to form the closed end of the preferred tubular containment member). The parts can be easily assembled without the need of adhesives or other fastening means for relatively low cost. Moreover, when filled, the device can be disposed of, in tact, with the removed needles stored therein.

By providing overlapping or interfitting guide means on the grasping members, a secure grasping of the needle hub by one hand is assured. In addition, a sufficient opening is provided to permit insertion of a needle and needle hub between the grasping members, yet the opening size is minimized for otherwise preventing access to the needles stored in the containment member.

Since the needles separated from their syringes are stored in the device with their needle tips pointing toward the closed end of the tube, there is virtually no chance that a needle point will protrude from the opening to risk accidental puncture. Further, by using the preferred relatively small-diameter tubular containment member for storing the removed needles, they will remain vertically aligned with their points facing the closed end.

By providing an integrally formed closure top, removed needles cannot fall out of the storage member once the top is closed. In addition, by forming the tube from at least a translucent material, it is easy to determine when the storage member is filled.

It will be appreciated by those skilled in the art that the foregoing brief description and the following detailed description are exemplary and explanatory of the invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

FIG. 2 is a side view of one of the grasping members shown in FIG. 1.

FIG. 3 is a side view of the other grasping members shown in FIG. 1.

FIG. 4 is a top plan view of the device shown in FIG. 1, showing the preferred interfitting between the two grasping members

DETAILED DESCRIPTION OF PREFERRED EMBODIMENT

Figure 1:
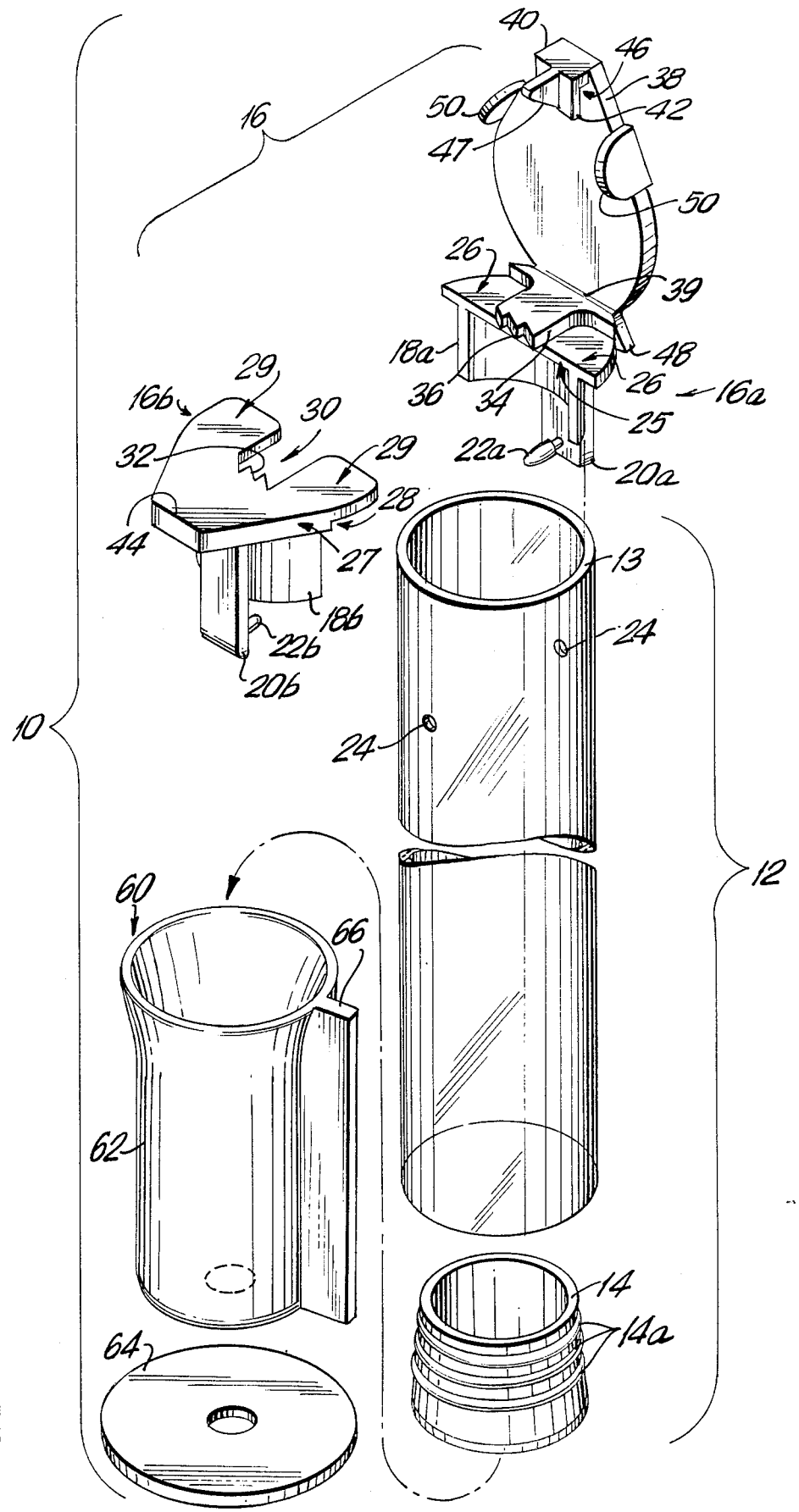
FIG. 1 is an exploded perspective view of a preferred embodiment of a needle removal/storage device according to the present invention.

Turning now to the accompanying drawings wherein like reference characters refer to like parts throughout the various views, there is shown in FIGS. 1-6, a preferred embodiment of a needle removal/storage device (indicated generally at 10) according to the present invention.

As here embodied, the needle removal/storage device includes a generally tubular storage or containment member 12 which is closed at one end and open at the other end. Advantageously and for ease and low cost of fabrication, the tubular containment member 12 may simply comprise a relatively small-diameter (e.g., 1"–1¾") tube section 13 which has a hollow, cup-like end cap 14 installed at one end to form the closed end of the tube. As preferably embodied, tube 13 is made by cutting sections from an "endless" extruded tube made of a flexible and resilient plastic material such as polyvinyl chloride to ensure that the tube continually returns to its original cylindrical configuration, even after repeated squeezing, as will be described more fully hereinafter.

In order to insure that end cap 14 cannot easily be removed, it is preferred that the end cap forms a tight friction fit with the interior walls of tube 13 and is recessed completely within the bottom edges of the tube section so that it has no readily accessible surface areas to permit removal from the tube. In addition, by relying on the tight friction fit between end cap 14 and the tube section 13, it will be appreciated that assembly of the containment member 12 can be easily accomplished simply by force fitting the end cap into one end of the tube section without requiring any complicated fasteners or any adhesive, thereby simplifying assembly. To enhance the friction fit, end cap 14 may include circumferentially extending ribs 14a. However, for ease of molding, ribs 14a can be eliminated so long as the center diameter of end cap 14 is proportioned to provide a snug friction fit within tube 13.

According to the invention, a closure assembly (indicated generally at 16) is mounted to the open end of tube 13 and is adapted both to close off the other end of the tube member and to grasp the hub of the needle portion of a hypodermic needle/syringe assembly for removal of the needle. Thus, as preferably embodied, the closure assembly 16 includes a pair of cooperating oppositely disposed jaw-like members which are adapted to grasp the hub of a needle to permit the needle to be separated from the syringe.

As here embodied, the closure assembly comprises a pair of grasping members (16a, 16b) mounted to the open end of the tube section 13 and operatively associated with each other to grasp the hub of a needle to be separated from its syringe. Advantageously, each grasping member is adapted for secure mounting to the tube end without requiring adhesives, screws or other separate fastening means to simplify assembly. To this end, each grasping member includes a generally arcuate wall section (18a, 18b) proportioned to conform generally to the interior configuration of the tube portion 13. It will be understood that arcuate walls 18a and 18b should extend less than a full semi-circle to permit sufficient reciprocating movement of the grasping members to grasp a needle hub, as will become more evident from the description below.

Each grasping member also includes a second wall member (20a, 20b) spaced from the arcuate wall sections (18a and 18b respectively) by a distance preferably equal to, or slightly greater than, the thickness of the wall making up tube 13. When the grasping members are mounted to the open end of tube 13, segments of the tube wall are thus sandwiched between each pair of wall members (i.e., arcuate walls 18a and 18b and second walls 20a and 20b, respectively).

In order to secure the grasping members 16a, 16b to the free end of tube 13 without the need for adhesive or separate fasteners (and thereby minimizing the number of parts needed to assemble the device), one of the wall members on each of the grasping members is formed with a rivet-like projection (22a, 22b) which is proportioned to lockably engage an opening 24 formed on opposite sides of tube 13. Locking projections 22a and 22b preferably project inwardly of tube 13 from wall members 20a and 20b, respectively, so as not to be accessible from the exterior of the device and thereby prevent a person from breaking them off and removing the grasping members to expose needles stored in the device.

As here embodied, projections 22a and 22b are each formed with a reduced diameter neck portion at its point of attachment to wall members 20a and 20b so as to define a relatively enlarged head which will become locked within the apertures 24 formed in the tube once pushed through the apertures That is, the projection head is forced through the opening until the reduced diameter neck resides within the opening; the thickened head portion will thus lock the grasping member in place. To this end, the diameter of the head portion is preferably slightly greater than the diameter of openings 24 to ensure that once forced through the openings, the head portion will resist any reverse force tending to push it back through the opening. Although the second walls 20a and 20b could also be formed in an arcuate configuration, it has been found that a straight wall segment works satisfactorily, is easier to form and economizes on material. As will be described more fully hereinafter, the straight wall sections 20a and 20b are preferably somewhat elongated to facilitate grasping by an operator's fingers when the grasping members are urged towards each other during the needle removal operation.

As indicated above, the grasping members provide cooperating jaw members for grasping the needle hub so that it can be unscrewed from the hypodermic syringe. Advantageously and as here preferably embodied, the grasping members also include interfitting guide means which cooperate to keep the jaw sections properly aligned relative to each other and assure a secure grip on the needle hub. To this end, one of the grasping members (here, member 16a) includes top wall member (indicated generally at 25) having a pair of recessed portions (each indicated at 26) which are formed on its upper surface and proportioned to permit slidable engagement with the other grasping member. The other grasping member (here, member 16b) includes a top wall member (indicated generally at 27) which is formed with a pair of correspondingly shaped recessed portions (each indicated at 28) formed on its bottom surface for permitting reciprocating slidable engagement with recessed portions 26.

Member 16b also includes a slot (indicated at 30) which thus forms a pair of projecting arms 29, with grasping teeth 32 (to be described more fully below) formed at the base of the slot 30. Correspondingly, recessed portions 26 formed in top wall 25 of member 16a provide a raised shoulder (indicated at 34) which is proportioned to fit within slot 30 during reciprocal slidable movement of the two grasping members 16a and 16b.

In order to insure easy relative sliding of projecting arms 29 over recessed portions 26, it is preferred that at least the tips of arms 29 engage a portion of slots 26 (FIG. 4) when the tube is not being used to remove a needle from a syringe and is in its original, unstressed configuration. Also advantageously, the inward edge of shoulder 34 includes saw-tooth gripping means 36 (to be described more fully below) which correspond in configuration to saw-tooth gripping means 32 on grasping member 16b.

Referring particularly to FIGS. 2-4, the grasping members further advantageously include vertical aligning means operatively associated between them for further facilitating reciprocal slidable movement between the grasping members. In the disclosed embodiment, one of the grasping members (here, grasping member 16b because its projecting arms 29 slide over the corresponding recessed portions 26 of member 16a) includes a pair of legs (each indicated at 29a) which project outwardly from arcuate wall 8b and extend generally parallel thereto to form a slot-like spacing (29b) between each projecting arm 29 and its corresponding leg 29a. This slot serves to receive the top member 25 of the other grasping member and restrain it from vertical movement. It will thus be appreciated that the additional legs 29a help guide the grasping members during their reciprocal movement relative to each other by sliding directly below the bottom surface of top member 25 to prevent vertical mis-alignment of the grasping members during use. Accordingly, legs 29a advantageously extend to about the same length as the projecting arms 29 and are preferably member 25 as possible. Advantageously, the slots 29b are slightly flared to form a funnel-like entry to facilitate receipt of top wall 25.

As preferably embodied, one of the grasping members (here grasping member 16a) is provided with an integrally formed top closure member 38 which is proportioned to releasably, lockably engage the other grasping member 16b for sealing the open end of tube 12 when the device is not being used to remove a needle from a hypodermic syringe and is, instead, serving its function of safely storing previously removed needles. To facilitate injection molding of the grasping members, top closure member 38 may be integrally formed with grasping member 16a by means of a "living hinge" attachment (indicated generally at 39).

As here embodied, the locking between top closure 38 and the other grasping member 16b is provided by a combination of latch-like flange members. Specifically, the front end of top closure 38 includes a downwardly projecting flange 40 from which projects, towards living hinge 39, a further projecting flange 42 which is spaced from the top closure member 38 by a distance at least equal to the thickness of projecting flange 44 formed on the back end of the other closure member (here, member 16b). Releasable locking can thus be carried out by squeezing the two grasping members 16a and 16b toward each other until the opposite facing edges of flanges 42 and 44 clear each other so that the top closure can lie flush against top wall member 27 on grasping member 16b. As the squeezing force exerted on the grasping members is released, flange 44 will be received within the slot (indicated at 46) formed between flange 42 and top closure 38, thereby locking top closure 38 against the other grasping member.

Advantageously and as preferably embodied, the releasable locking member includes ramp-like gusset member 47 to effectively form a sear and lip lockable engagement means with flange 44. Thus, when closure is desired, one need only push down on cover member 38 until gusset 47 engages the edge of flange 44. Thereafter, continued downward pressure on cover 38 causes flange 44 to move inwardly as it rides along the canted surface of gusset 47, causing the tube to become deformed slightly, until it reaches the edge of flange 42. After the oppositely facing edges of flanges 42 and 44 pass each other due to further continued downward pressure on cover 38, flange 44 will "snap" into slot 46 due to the radially outward force exerted by the resilient tube member, thereby locking cover 38 to member 16b.

Also advantageously, top closure 38 preferably includes an additional flange (indicated at 48) which projects from the opposite side of hinge 39 for facilitating single hand operation of the entire device. Thus, when use of the device to remove a needle is desired, a person simply squeezes the two grasping members toward each other until the opposite edges of flanges 42 and 44 clear each other. The person can then use one of his or her fingers (the index finger as shown in FIG. 6) to pull down on flange 48, thereby causing the other side of top closure 38 to be rotated upwardly and expose the entry opening (indicated at 31 in FIG. 4) to the device.

Similarly, when the device is to be closed, the person pushes up on flange 48 to rotate the other end of top closure down against the other grasping member. The grasping members are squeezed together (either by manual force, or through the action of canted gusset 47 urging flange 44 Q inwardly, all as described above) until the opposite edges of flanges 42 and 44 clear each other and flange 44 is aligned with slot 46, whereafter flange 44 snaps into, and becomes locked within, slot 46.

In order to maintain proper alignment between flanges 42 and 44, particularly when the device is in the locked configuration, both the top closure 38 and the corresponding portion of top wall member 27 have essentially the same configuration when seen from a top plan view. In addition, top closure 38 preferably has a pair of retaining tabs 50 depending from its peripheral edge portions to maintain top closure 38 and the opposite grasping member (16b) in fixed positions relative to each other and thereby maintain their alignment while in the closed configuration. Thus, the locking provided between flanges 42 and 44 cannot be overridden by sliding the top closure 38 and grasping member 16b sideways relative to each other.

Figure 5:
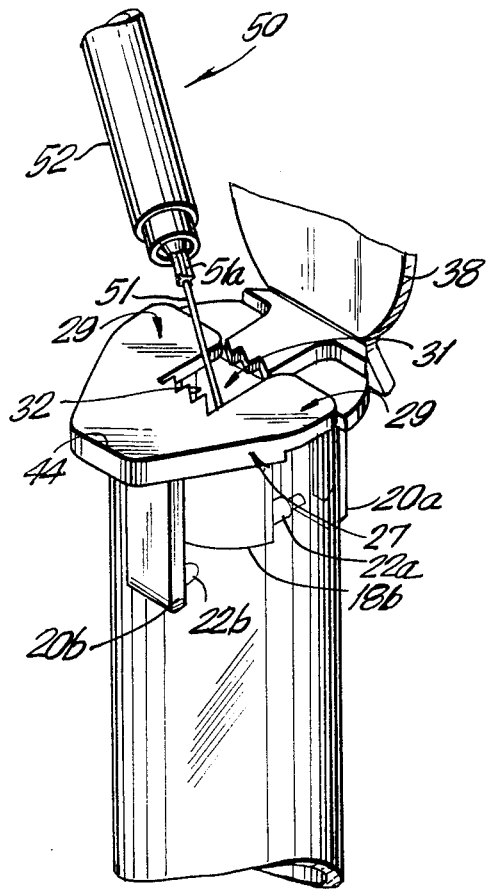
FIG. 5 is a perspective view of the top portion of the device shown in FIG. 1, illustrating initial insertion of a needle during the needle removal operation.
Figure 7:
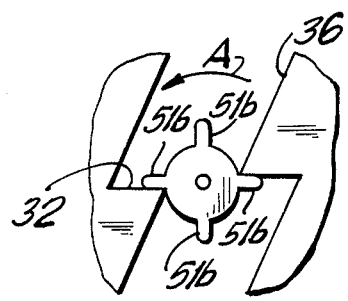
FIG. 7 is a plan view showing the preferred sawtooth grasping means engaging the hub of a needle to be removed.
Figure 6:
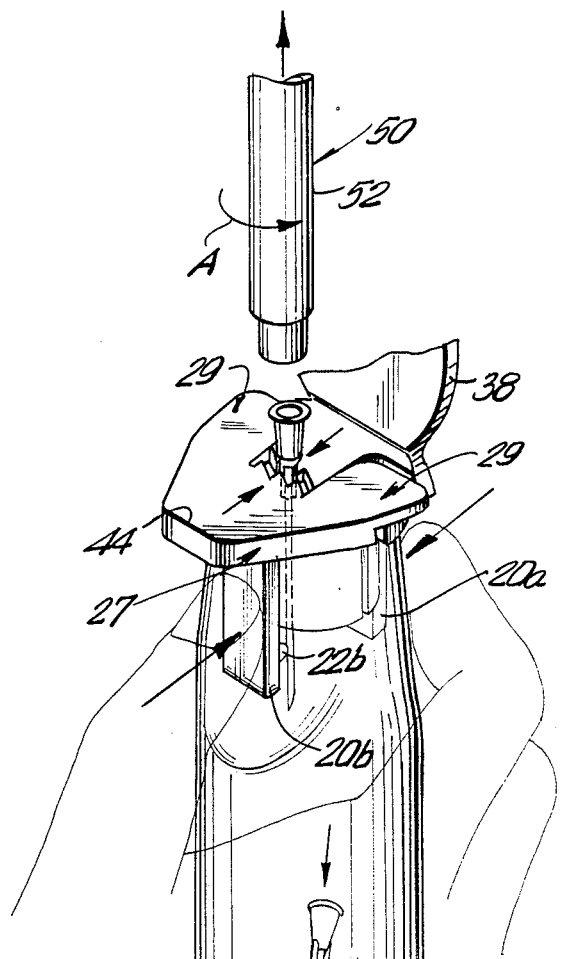
FIG. 6 is a view similar to FIG. 5 (except the entire device is depicted) illustrating how the needle removal operation is completed.

Turning then to FIGS. 5–7, there is shown a perspective view of the invention illustrating its operation in the removal of a needle from a hypodermic syringe. To begin the needle removal operation, the device can be conveniently held in one hand while the needle is held in the other. The top closure 38 is first opened as described above to expose entry opening 31. Once the top is opened, the user inserts the needle point through opening 31 until the ribbed portion (described below with reference to FIG. 7) of needle hub (51a) is about even with the saw tooth gripping members 32 and 36. The user then squeezes the grasping member 16a and 16b toward each other (preferably by exerting the squeezing force on walls 20a and 20b) until the needle hub is firmly grasped between the two saw-tooth gripping members. The user then removes the hypodermic syringe from the needle by turning it in the direction indicated by the arrow A in FIGS. 6 and 7.

FIG. 7 illustrates an exaggerated view of the engagement between the needle hub and the saw-teeth of the grasping members. It will be appreciated that by using the left-to-right inclining saw-tooth configuration shown herein, there is no need to squeeze hard on the grasping members so long as the teeth engage the circular protrusions or ribs (51b) formed on the needle hub. (If the sloped portion of the teeth face the other direction, the needle hub might simply rotate as the syringe is turned by the user.) Whether the needle is threaded into the syringe or simply friction fit, the foregoing turning operation will cause separation of the needle and syringe.

Once the syringe is detached from the needle, the user simply releases his or her grip on the grasping members to allow them to return to their original positions due to the resilience of the tube member 13. The needle will simply drop, by its own weight, into the containment member formed by tube 13 and end cap 14. When the needle is safely contained within the containment member, the user should seal the device by rotating cover member 38 back into its closed configuration substantially as described above. Again, the flange 48 provides a convenient lever for the user to rotate the top closure 38 downwardly by a simple upward push on the bottom of flange 48, all in a single-handed operation.

Referring back to FIG. 1, there is shown an additional feature according to the present invention. According to this aspect, a cup-like stand (indicated generally at 60) is provided for holding the device 10 vertically upright. Stand 60 is particularly useful for enabling initial insertion of a needle point into the device without the need for holding the device, a practice recommended by C.D.C.. (Once the needle point is inserted, the device is picked up by the user's other hand to perform the needle removal operation, etc.) Stand 60 includes a cylindrical cup portion 62 proportioned to receive the closed end of device 10 and support it so as to stand erect. The stand also includes a relatively enlarged diameter disc 64 which provides a stand/base for the cup portions It will thus be understood that when the device 10 is received within stand 60, the device will be supported upright while, e.g., top closure 38 is opened and the tip of a needle to be removed is initially inserted. Thereafter, the device can be operated by the other hand, substantially as described above.

The cup and disc can be formed as separate but interlocking parts to permit the cup portion to be mounted to a bracket (not shown) on, e.g., a medical cart. To this end, a flange (indicated at 66) may be formed on the cup to slide within an appropriately formed bracket. As shown in Figure I, only one side of flange 66 is visible but it will be understood that it is symmetrical.

Also advantageously and for convenience in transporting the device 10, a pocket clip member (indicated at 54 in FIG. 3) may be formed on one of the grasping members. As here embodied, clip 54 is formed by a relatively short projection 54a and a relatively elongate flange 54b projecting parallel to the second wall 20a of grasping member 16a. It will be found that the tube may be conveniently suspended from the user's shirt pocket, belt or other piece of garment so that the needle removal/storage device according to the present invention is readily available whenever the user needs it.

The particular configuration of component parts for the present invention are particularly advantageous in that they can be made by conventional fabrication techniques and can be easily assembled without requiring extraneous parts or operations. Thus, as indicated above, tube member 13 can be formed by cutting sections from an extruded tube. The grasping members and the end cap can be injection molded from any injection moldable material, preferably one which is capable of forming a living hinge such as polypropylene.

It will be appreciated by those skilled in the art that the present invention in its broader aspects is not limited to the particular embodiments shown and described herein, and that variations may be made which are within the scope of the accompanying claims without departing from the principle of the invention and without sacrificing its chief advantages. Thus, for example, while the disclosed embodiment includes interfitting guide means in the form of overlapping members (e.g., arms 29 and recesses 26 plus legs 29a), this arrangement is advantageous from the standpoint of facilitating molding but any guide/restraining means may be used which achieve the purposes set out herein. Similarly, any releasable locking means between cover 38 and grasping member 16b may be used, but a sear-and-lip type arrangement is preferred because of its ease of operation.

What is claimed is:

1. A needle removal and storage device for removing needles from hypodermic needle/syringe assemblies and automatically receiving and safely storing removed needles within the device, comprising:
 a storage/containment member which is closed at one end and proportioned to receive used needles; and
 a top assembly at the open end of the storage/containment member and providing an opening to receive a needle and its hub portion, said top assembly including a pair of grasping members, said grasping members being mounted directly to generally opposite sides of the storage/containment member at its open end, said grasping members being proportioned to receive the hub portion of the needle to be removed from its syringe yet to provide substantial closure of said open end, said device being adapted to permit said grasping members to constrict said opening when squeezed together by a person holding said device so as to grasp the needle hub at its ribbed portion for removal of the needle from its syringe, such that when a needle is inserted and received within the opening of said top assembly, a person may grasp the needle hub by squeezing said grasping members and remove the hypodermic syringe from the needle, whereafter the grasp on the needle may be released to permit the needle to drop vertically into the storage/containment member, needle point first, for automatic safe storage of used needles until the entire device is ultimately disposed of.

2. A needle removal and storage device for removing needles from hypodermic needle/syringe assemblies and automatically receiving and safely storing removed needles within the device, comprising:
 a storage/containment member which is closed at one end and open at the other end and proportioned to receive used needles; and
 a top assembly at the open end of the storage containment member and providing an opening to receive a needle and its hub portion, said top assembly including a pair of grasping members mounted to generally opposite sides of the storage/containment member at its open end, and proportioned to receive the hub portion of the needle to be removed from its syringe, said grasping members adapted to be moved toward and away from each other in generally reciprocating vice-like fashion such that when a needle is inserted and received within the opening of said top assembly, a person may squeeze the grasping members to constrict said opening so as to grasp the needle hub at its ribbed portion for removal of the hypodermic syringe from the needle, whereafter the grasp on the needle may be released to permit the needle to drop vertically into the storage/containment member, needle point first, for automatic safe storage of used needles until the entire device is ultimately disposed of, said storage/containment member being generally flexible and resilient at its open end to permit said grasping members to be urged towards each other yet to resiliently bias said grasping members away from each other after the grasping force is released.

3. A device according to claim 2 wherein said storage member comprises a generally tubular member made of a pliable and resilient plastic material.

4. A device according to claim 3 wherein said closed end of said storage chamber is formed by force-fitting a cup-like end cap into one end of said tubular member, said end cap being proportioned to fit snugly within the interior walls of the tube-like storage member to form a secure force fit, and said end cap being fully received and enclosed within the exterior walls of the tubular member to prevent removal of the end cap.

5. A device according to claim 3 wherein said grasping members include interfitting guide means proportioned and positioned to overlap each other at least during the needle removal operation so as to prevent a loss of grip on the needle while the needle is being separated from the syringe.

6. A device according to claim 5 wherein said interfitting guide means overlap each other even when said device is not being squeezed to remove a needle to minimize the opening provided between said grasping members to the interior of said storage member.

7. A device according to claim 6 wherein said interfitting guide portions include at least one projecting arm portion formed on one of said grasping members and a correspondingly proportioned recessed portion formed in the other grasping member, each said arm portion and each said recessed portion being adapted for reciprocating slidable relative movement when said grasping members are squeezed toward each other and released to move away from each other.

8. A device according to claim 7 which includes a pair of said projecting arm members formed on said one grasping member and a pair of said recessed portions formed on said other grasping member, said projecting arm members providing a notch-like cut out therebetween to permit insertion of a needle and needle hub to be removed from a syringe, and wherein said two recessed portions define a raised shoulder portion which is proportioned to fit within the notch-like cut out formed between the two projecting arm members.

9. A device according to claim 8 wherein said notch-like slot and said raised shoulder have oppositely facing grasping edges which are formed with saw tooth gripping means for securely grasping the needle hub of the needle to be removed from its syringe.

10. A device according to claim 2, wherein said top assembly also includes closure means for securing the needles within the storage/containment member and preventing access into the storage member.

11. A device according to claim 10 wherein said closure member comprises a closure panel formed integrally with one of said grasping members and attached thereto by a living hinge-type connection.

12. A device according to claim 11, wherein said top closure member further includes releasable locking means for releasably lockably engaging the other grasping member to hold said top member securely closed over the open end of the storage member when said device is not being used for removal of a needle.

13. A device according to claim 12, wherein said releasable locking means comprise a first flange formed on said top closure member and a second flange projecting from the other grasping member, said first flange spaced from said closure member by a distance at least equal to about the thickness of said second flange to permit said second flange to be captured between said first flange and said top closure member.

14. A device according to claim 13, wherein said top closure member further includes a third flange projecting in a direction opposite that from said top closure member relative to said living hinge to permit opening and closing of said top closure member by simple finger manipulation by the user to insure that the device can be fully operated when held in one hand while the needle/syringe assembly is held in the other hand.

15. A device according to claim 13, wherein, said releasable locking means further includes a gusset member on said first flange, said gusset member providing a canted surface which engages said second flange to form a sear-and-lip type releasable locking.

16. A device according to claim 3, wherein each said grasping means includes a generally arcuate wall member and a second wall member spaced apart by a sufficient distance to receive a wall portion of said tubular member therebetween, one of said wall members having a bead-like projection adapted to be lockably received within an opening in said tubular member to secure said grasping member to said tubular member.

17. A device according to claim 2, which further includes cup-like stand means for holding said device upright to permit initial insertion of a needle point into said opening provided by said top assembly without requiring a person to hold the device.

* * * * *